United States Patent [19]
Tymchuck

[11] Patent Number: 6,145,373
[45] Date of Patent: Nov. 14, 2000

[54] FOOD VISCOMETER AND METHOD OF USE

[75] Inventor: Donald L. Tymchuck, Minnetonka, Minn.

[73] Assignee: Med-Diet Laboratories, Inc., Plymouth, Minn.

[21] Appl. No.: 09/172,961

[22] Filed: Oct. 14, 1998

[51] Int. Cl.[7] .................................................. G01N 11/14
[52] U.S. Cl. ...................... 73/54.28; 73/54.31; 73/54.35
[58] Field of Search ............................... 73/54.28, 54.29, 73/54.31, 54.32, 54.35

[56] References Cited

U.S. PATENT DOCUMENTS

| | | |
|---|---|---|
| 1,321,736 | 11/1919 | Green . |
| 1,449,458 | 3/1923 | Sutermeister . |
| 1,942,920 | 1/1934 | Fawkes . |
| 2,237,743 | 4/1941 | McIntyre .............................. 73/54.31 |
| 2,679,157 | 5/1954 | Carpenter . |
| 3,090,222 | 5/1963 | Akaboshi et al. . |
| 3,316,754 | 5/1967 | Nagatsuka et al. . |
| 3,803,903 | 4/1974 | Lin . |
| 3,875,791 | 4/1975 | Fitzgerald et al. . |
| 4,299,119 | 11/1981 | Fitzgerald et al. . |
| 4,484,468 | 11/1984 | Gau et al. . |
| 5,052,593 | 10/1991 | Grome et al. . |
| 5,503,003 | 4/1996 | Brookfield .............................. 73/54.32 |

FOREIGN PATENT DOCUMENTS

| | | | |
|---|---|---|---|
| 2738290 | 3/1979 | Germany .............................. | 73/54.28 |
| 0691025 | 5/1953 | United Kingdom .................. | 73/54.35 |

*Primary Examiner*—Daniel S. Larkin
*Attorney, Agent, or Firm*—Craig J. Lervick Oppenheimer, Wolff & Donnelly LLP

[57] ABSTRACT

The food viscometer of the present invention includes a microprocessor controlled fluid viscometer assembly contained in a housing configured for easy mounting on the upper edge of a glass or other conventional drinking utensil. Projecting from the housing of the food viscometer is a probe that is placed in the liquid contained in the liquid container. The housing adjustably engages a base assembly that permits raising and lowering of the housing to ensure that the probe is placed a predetermined depth into the liquid. The base assembly also securely engages the upper edge of the liquid container to ensure the generally vertical positioning of the probe within the liquid, and also to ensure that the probe is spaced a predetermined minimum distance from the edges of the liquid container.

33 Claims, 6 Drawing Sheets

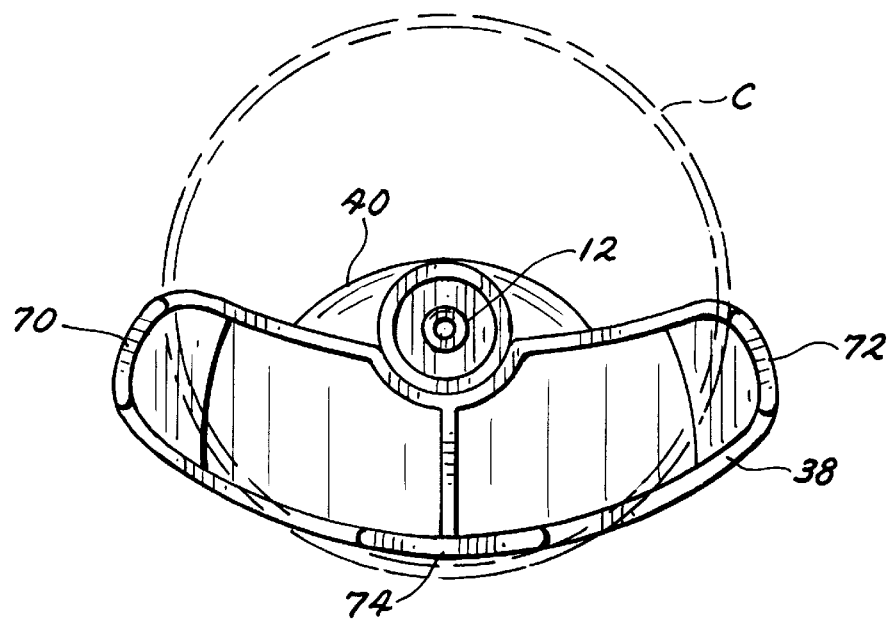
FIG. 4
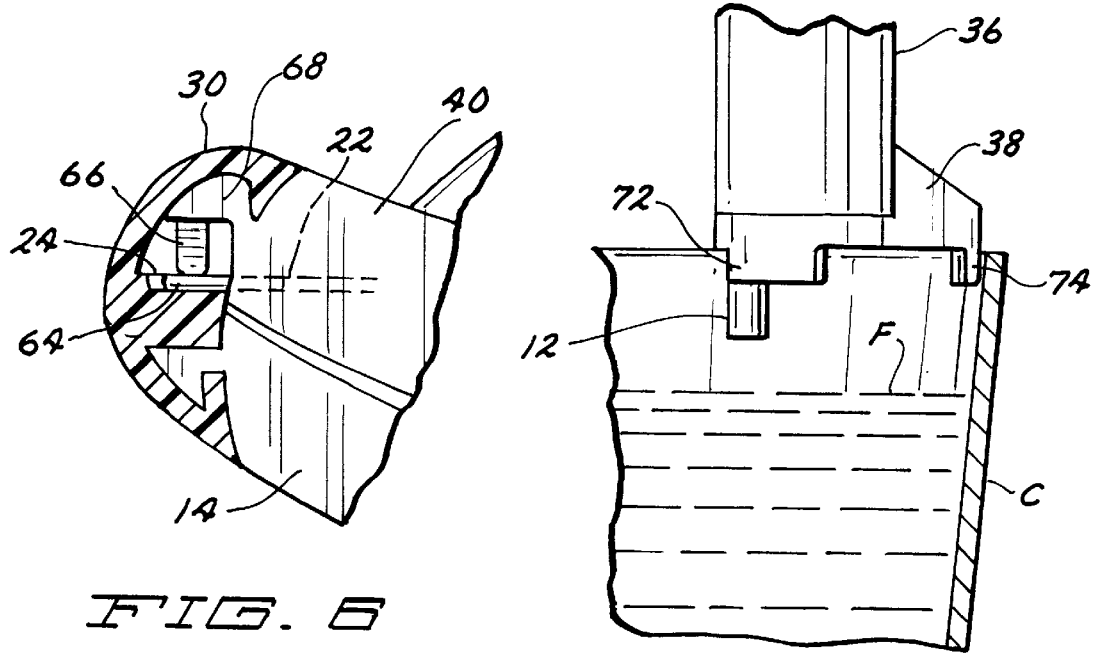
FIG. 6
FIG. 5

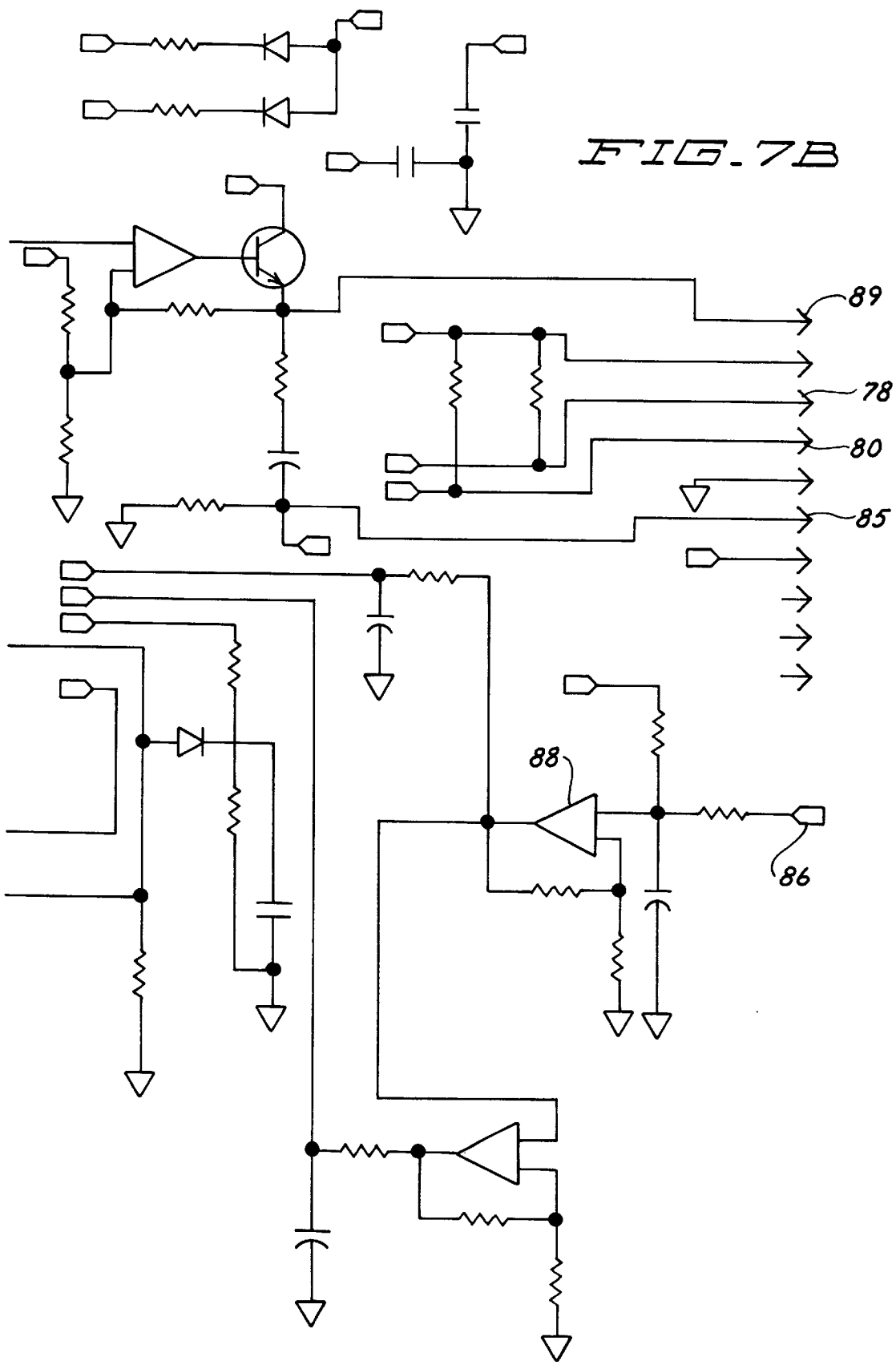

FOOD VISCOMETER AND METHOD OF USE

BACKGROUND OF THE INVENTION

The present invention relates generally to rotational viscometers for measuring the viscosity of a fluid, and in particular to a rotational viscometer for measuring the viscosity of nutritional liquids for people suffering from dysphagia.

Rotational viscometers for measuring the viscosity of fluids are well known, and have been used for a wide variety of applications, generally industrial in nature. However, only in recent years has attention been focused on the needs of patients suffering with the condition known as dysphagia. Dysphagia is a physical condition, usually the result of a trauma to the body, such as an accident or a stroke, that is manifested by a difficulty in swallowing. As with many other physical conditions, dysphagia may be more or less severe for different patients, and may improve or worsen over time for a particular patient.

Methods of measuring the severity of dysphagia for a particular patient are under development to classify accurately the degree of severity of that patient's condition for purposes of developing treatments and diets best suited to the patient's condition. Of particular interest is the development of a diet that provides nutritional foods which may be swallowed by the dysphagia patient without the risk of choking or other negative responses resulting from the patient's swallowing disorder. Presently, four fluid viscosity groupings are generally recognized to reflect the various degrees of severity of dysphagia. These four groupings are: thin; nectar like; honey like; and spoon thick. Examples of foods that fall in these categories range from broth in the thin grouping to puree in the spoon thick category.

As noted above, various viscometers have been used for a variety of applications in the past. However, these have not been available for easy, portable use. Further, prior art viscometers have not provided the capability to detect three break points and determine which of the four resulting zones a viscosity reading falls within, and then give a visual indication of which such zone contains the resulting reading.

The food viscometer of the present invention overcomes difficulties described above and affords other features and advantages heretofore not available.

SUMMARY OF THE INVENTION

The food viscometer of the present invention includes a microprocessor controlled fluid viscometer assembly contained in a housing configured for easy mounting on the upper edge of a glass or other conventional drinking utensil. Projecting from the housing of the food viscometer is a probe that is placed in the liquid contained in the liquid container. The housing adjustably engages a base assembly that permits raising and lowering of the housing to ensure that the probe is placed a predetermined depth into the liquid. The base assembly also securely engages the upper edge of the liquid container to ensure the generally vertical positioning of the probe within the liquid, and also to ensure that the probe is spaced a predetermined minimum distance from the edges of the liquid container.

The probe of the food viscometer may be a straw or rod, which is replaceably detachable from a clamping means on the housing. A motor in the housing spins the probe at a predetermined rate, and the microprocessor measures the electrical current used by the motor. The current used by the motor while the probe is positioned in the liquid is compared to the current used by the motor to turn the probe before placing the probe in the liquid, and the viscosity of the liquid is calculated based on this measurement.

It is an object of the present invention to provide a viscometer for easily and accurately determining the viscosity range of liquid foods for service to patients suffering from dysphagia. It is a further object of this invention to provide such a food viscometer that is simple to use, and controls many of the external factors that might otherwise lead to inaccurate viscosity readings. It is a further object of this invention to provide an accurate, objective measurement standard for measuring the viscosity range of liquid foods. It is also an object of this invention to reduce costs related to thickeners, packaged liquids, and errors resulting from attempts to prepare a proper diet for patients suffering from dysphagia. It is yet a further object of this invention to promote better patient hydration and nutrition, and to improve patient care and satisfaction.

Other objects and advantages of the invention will become apparent from the following detailed description and from the appended drawings in which like numbers have been used to describe like parts throughout the several views.

BRIEF DESCRIPTION OF THE DRAWINGS

FIG. 4 is a bottom view of the food viscometer taken along line 4—4 of FIG. 3A;

FIG. 5 is a side view of the base assembly engaging the upper edge of the liquid serving container;

FIG. 6 is a section view of the base assembly taken along line 6—6 of FIG. 3B; and FIGS. 7A and 7B are first and second portions, respectively, of an electrical schematic of the food viscometer.

DETAILED DESCRIPTION OF PREFERRED EMBODIMENTS

Figure 1:
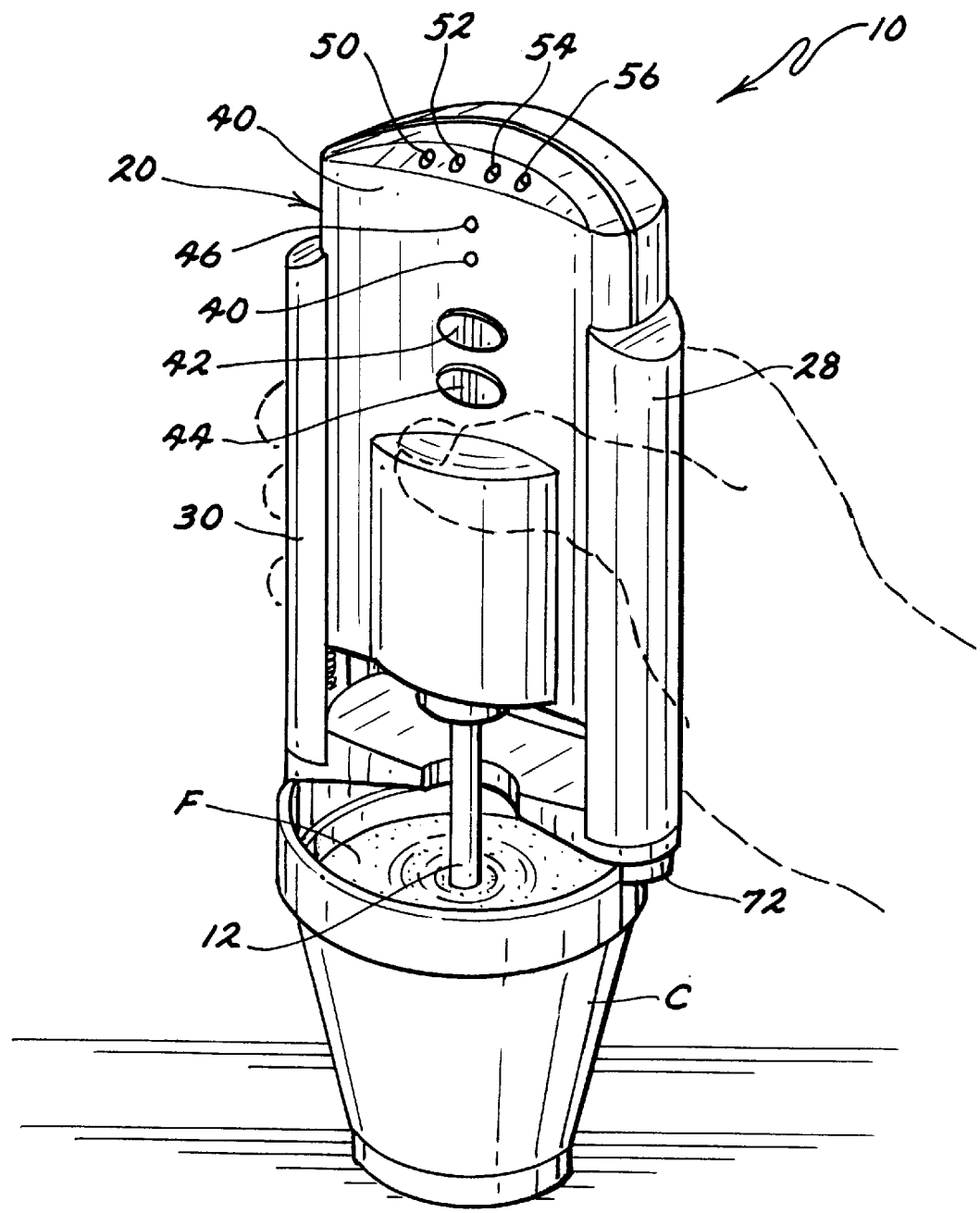
FIG. 1 is a is a perspective view of the food viscometer of the present invention.

With reference to the drawings, and in particular to FIG. 1, the food viscometer of the present invention is generally indicated by reference numeral 10. Food viscometer 10 includes a probe 12 attached thereto to be immersed a predetermined distance, preferably approximately two inches, into a fluid F contained in a cup or other beverage container C.

Figure 2:
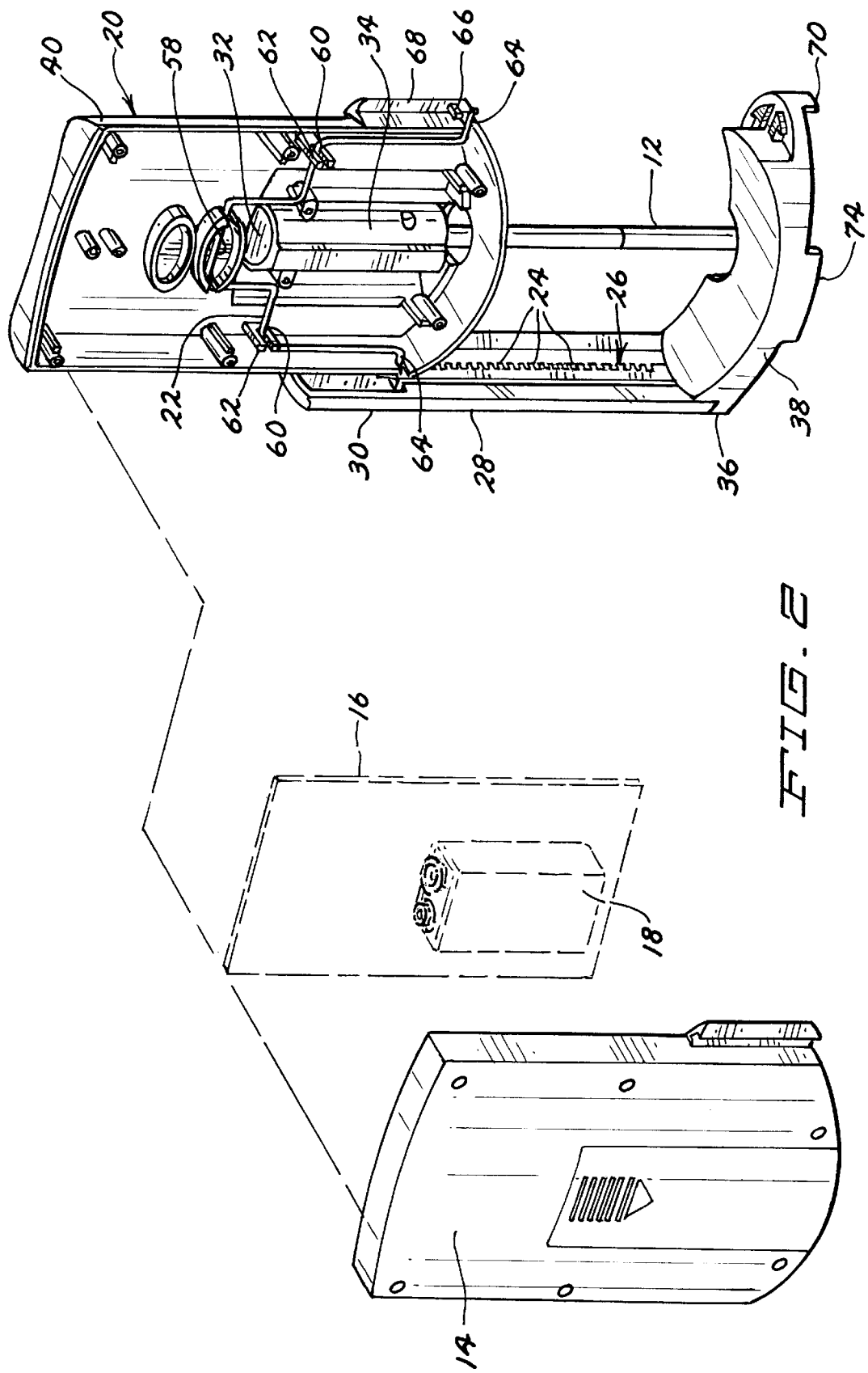
FIG. 2 is a rear exploded perspective view of the food viscometer showing the base assembly in the fully extended position.
Figure 3:
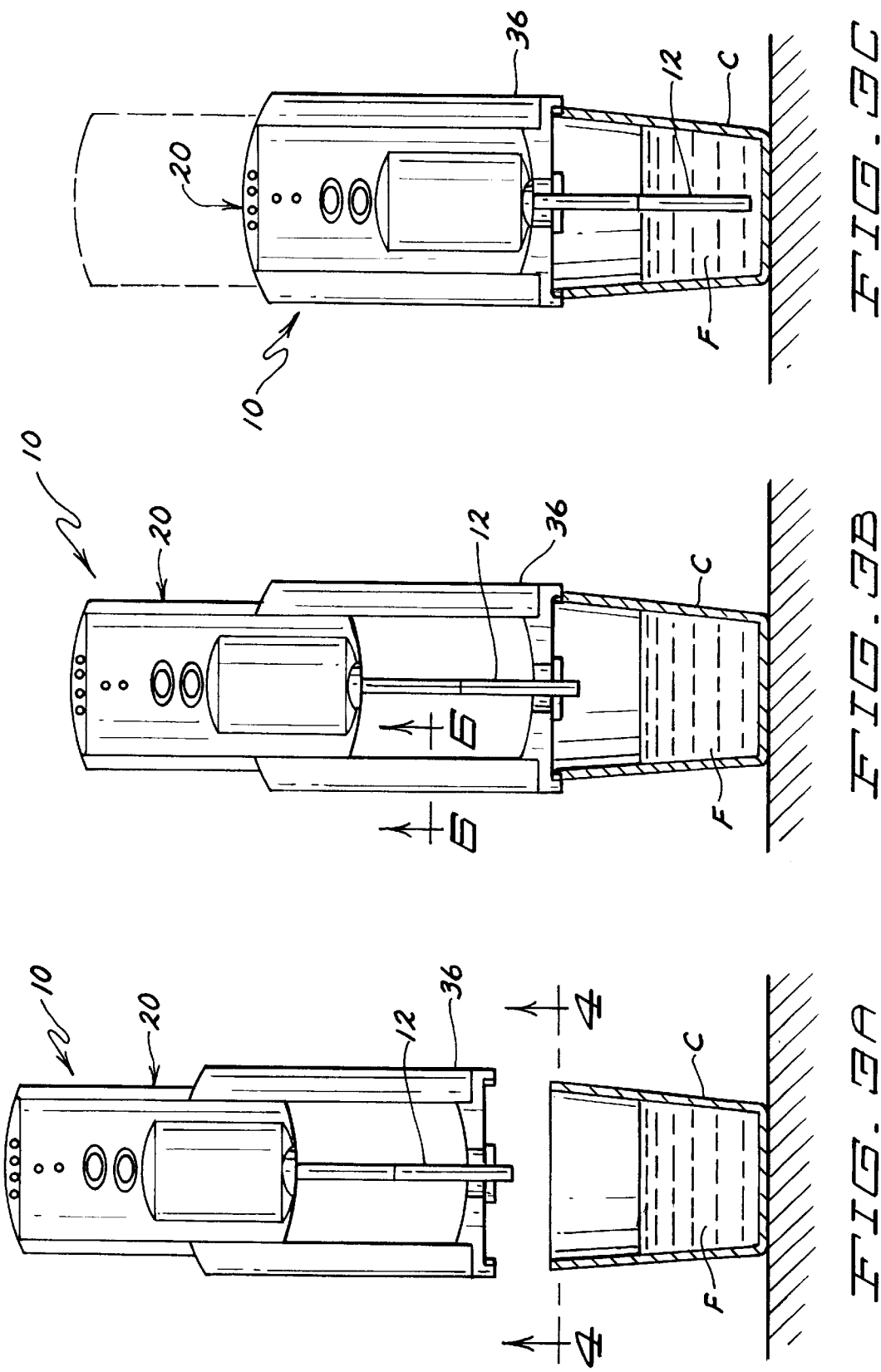
FIGS. 3A, 3B and 3C are front views of the food viscometer showing the food viscometer in position for engaging the upper edge of a liquid serving container, resting on the upper edge of the liquid serving container, and lowered for the probe to engage the liquid contained in the container, respectively.

Referring to FIG. 2, food viscometer 10 includes a rear panel 14, a circuit board 16, and a battery 18. Power may also be provided from an AC adapter, not shown. Housing 20 also contains spring lever 22 engaging ratchet teeth 24 of ratchet tooth assemblies 26 of right and left columns 28, 30, respectively. A motor 32 is contained within motor cover 34. Motor 32 is releasably linked to probe 12 by conventional means. Columns 28, 30 support and are a part of adjustable base assembly 36, which also includes base member 38.

Referring again to FIG. 1, front panel 40 includes projecting therefrom a test button 42 and a position button 44.

Several signal lights are also displayed on front panel 40, including a wait status indicator 46 and a ready status indicator 48. Across the top of front panel 40 are also four additional indicators showing the result of the viscometer reading by indicating which of the four groupings the liquid being tested falls into. First indicator 50 indicates the liquid is thin; second indicator 52 indicates the liquid is nectar like; third indicator 54 indicates the liquid is honey like; and fourth indicator 56 indicates the liquid is spoon thick. Each indicator is a preferably a different color light source, such as a light emitting diode, with color preferably including red for first indicator 50, yellow for second indicator 52, blue for third indicator 54, and green for fourth indicator 56. Preferably, test button 42, position button 44, and indicators 46, 48, 50, 52, 54, and 56 are labeled with an appliqué or engraved label attached or molded to front panel 40 for easy identification of the meaning of the various indicator lights.

Referring to FIGS. 1, 2, 3A, 3B, and 3C, housing 20 is vertically adjustable relative to base assembly 36 through the interaction of spring lever 22 and ratchet teeth 24 of ratchet tooth assembly 26. As most clearly illustrated in FIG. 2, spring lever 22 is positioned within housing 20 so that its central portion 58 is located immediately behind position button 44 of front panel 40. Intermediate portions 60 of spring lever 22 are hingedly retained within boss pairs 62 projecting from the rear of front panel 40. Thus, when position button 44 is depressed, central portion 58 of spring lever 22 is shifted away from front panel 40, and end portions 64 of spring lever 22 pivot in a direction opposite that of central portion 58, thereby becoming disengaged from ratchet teeth 24 of ratchet tooth assemblies 26 of right and left columns 28, 30 of base assembly 36. With end portions 64 of spring lever 22 thus disengaged, housing 20 may be freely vertically adjusted relative to base assembly 36 until a desirable position is reached, at which time position button 44 is released.

Reference to FIGS. 2 and 6 shows a stability spacer 66 which projects from the inner surface of front panel inner rail portion 68. Stability spacer 66 bears against but never extends between ratchet teeth 24 of ratchet tooth assemblies 26 to prevent rotational motion of housing 20 relative to base assembly 36. Housing 20 includes front panel inner rail portions 68 on the right and left sides of front panel 40, and each front panel inner rail portion 68 includes a stability spacer 66.

Reference to FIGS. 4 and 5 shows the left, right, and intermediate projecting portions 70, 72, 74, respectively, of base member 38. For proper operation of food viscometer 10, it is important to maintain the position of probe 12 at least one inch from all generally vertical sides of beverage container C. Projecting portions 70, 72, 74 are spaced in such a manner to permit easy positioning of food viscometer 10 on the upper edge of beverage container C with probe 12 appropriately positioned an adequate distance from the generally vertical walls thereof.

Figure 7A:
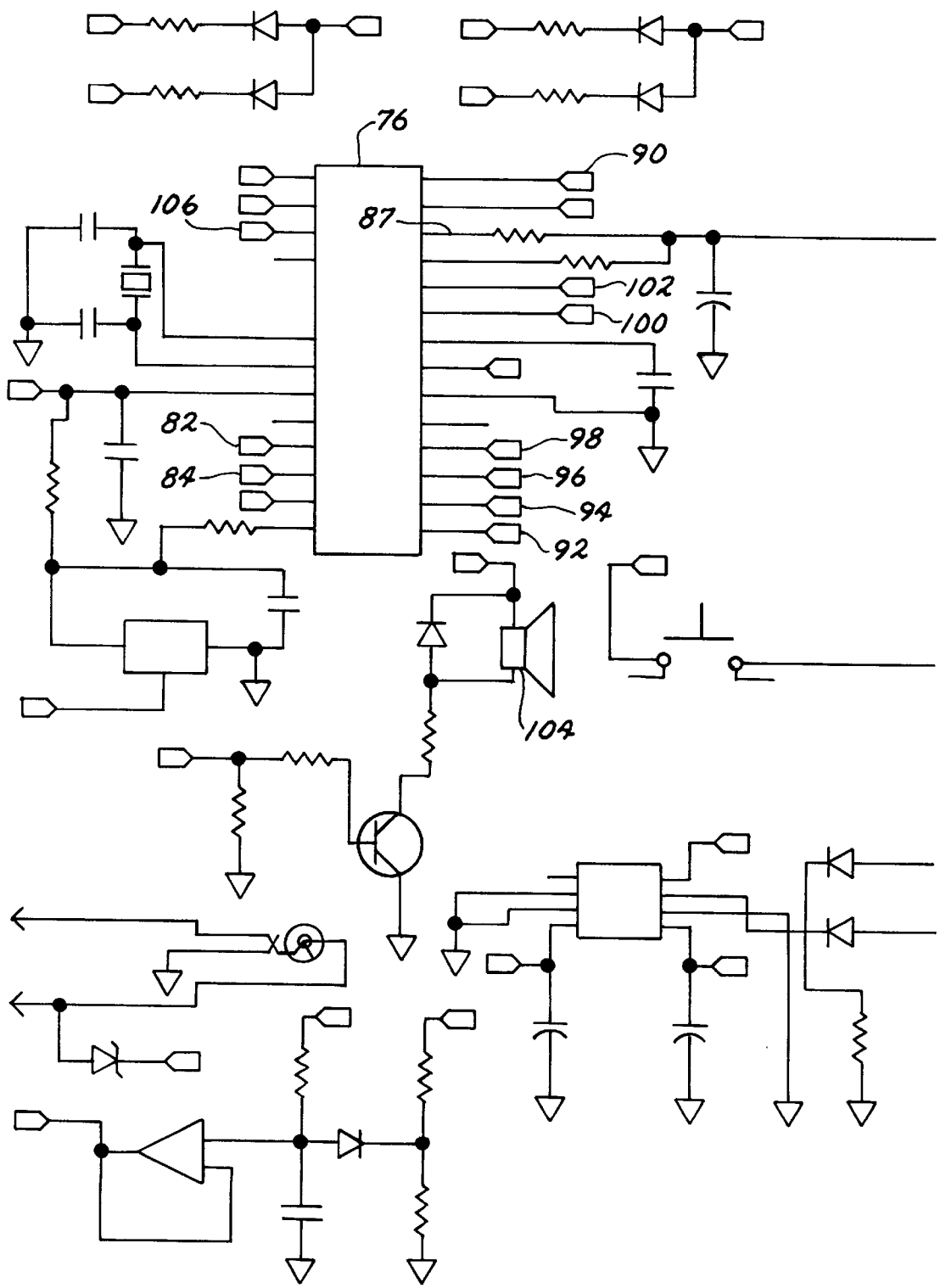

With reference to FIGS. 7A and 7B, disclosed therein are the electronics found on circuit board 16 for controlling motor 32, responding to various inputs and determining various outputs. In particular, circuit board 16 includes a microprocessor 76 that controls the functions of food viscometer 10. Lines 78 and 80 represent output signals from an encoder controlling the speed of motor 32, which signals are input to microprocessor 76 at 82, 84 respectively. Line 86 represents motor current input, originating from line 85, which is amplified by amplification circuit 88, the output from which is detected by microprocessor 76 at line 90. Microprocessor 76 analyzes signals from the encoder to ensure that motor 32 is operating at approximately 240 rpm, although a +/−10% deviation is considered acceptable for proper operation of food viscometer 10. Feedback from microprocessor 76 to adjust the speed of motor 32 is transmitted from line 87 and fed through the motor connector at line 89. Microprocessor 76 also analyzes motor current to determine resistance to spinning probe 12, and thereby calculate the viscosity of the fluid F in container C. Based on the results of this calculation, microprocessor 76 sends a signal to illuminate one of the indicators 50, 52, 54 or 56. Line 92 indicates the output from microprocessor 76 to indicator 50, line 94 indicates the output to indicator 52, line 96 indicates the output to indicator 54, and line 98 indicates the output to indicator 56.

Prior to each use of food viscometer 10, the unit must be calibrated to obtain an accurate measurement. The calibration process is simple, requiring only that before positioning probe 12 into fluid F, the user press test button 42, at which time wait status indicator 46 will illuminate. When calibration is complete, ready status indicator 48 will illuminate and a beep will sound. Food viscometer 10 is now calibrated and ready for use. The output from microprocessor 76 to wait status indicator 46 is indicated by line 100, and the output to ready status indicator 48 is indicated by line 102. The output to beeper 104 is indicated by line 106.

The steps for use following calibration are equally straightforward. Food viscometer 10 is positioned above beverage container C, with base member 38 resting on the upper edge thereof as illustrated in FIG. 5, and probe 12 extending into fluid F. Holding base assembly 36 in position, the user presses position button 44 and raises or lowers housing 20 relative to base assembly 36 until probe 12 extends into fluid F approximately two inches. It is important that probe 12 not contact the bottom surface of beverage container C, and it is preferable that there be at least a 0.25 inch space therebetween. Further, it is preferred that the diameter of probe 12 be approximately 0.25 inch, and it is important that the inside diameter of beverage container C be at least approximately 2.125 inches. Once probe 12 extends to the proper depth in fluid F, position button 44 may be released, and the user may press test button 42. Microprocessor 76 actuates motor 32, analyzes feedback from the encoder and amplification circuit 88, determines the viscosity of fluid F, illuminates one of the appropriate indicators 50, 52, 54, or 56, and instructs beeper 104 to beep twice.

Those skilled in the art will further appreciate that the present invention may be embodied in other specific forms without departing from the spirit or central attributes thereof. In that, the foregoing description of the present invention discloses only exemplary embodiments thereof, it is to be understood that other variations are contemplated as being within the scope of the present invention. Accordingly, the present invention is not limited in the particular embodiments which have been described in detail therein. Rather, reference should be made to the appended claims as indicative of the scope and content of the present invention.

What is claimed is:

1. A process for measuring the viscosity of a potable liquid contained in a beverage container using a food viscometer having a body, a base section vertically adjustable relative to the body and having a lower surface for resting contact with the upper edge of the beverage container, and a probe for insertion into the potable liquid, the process comprising the steps of:

calibrating the food viscometer;

positioning the lower surface of the base section securely against the upper edge of the beverage container;

adjusting the height of the body of the food viscometer relative to the base section of the food viscometer so that the probe extends a predetermined distance into the potable liquid contained in the beverage container;

actuating the food viscometer; and reading the display of the food viscometer to determine the viscosity of the potable liquid contained in the beverage container.

2. A device for measuring the viscosity of food substances contained within an open container, the device comprising:

a housing;

a base assembly adjustably attached to said housing, said base assembly having an engagement portion for engaging the opening of the food substance container;

a probe member protruding from said housing;

a motor within said housing for rotating said probe member at a constant rotation rate, said motor having an output portion;

a sensor in said housing for detecting the operational characteristics of said motor; and a display on said housing for displaying a viscosity level based on the readings obtained by said sensor.

3. The viscosity measuring device defined in claim 2, wherein said base assembly further comprises:

right and left attachment members for adjustable attachment of said base assembly of said housing, respectively.

4. The viscosity measuring device defined in claim 3, wherein said base assembly further comprises:

a base member extending between said right and left attachment members, said base member having a front edge, a rear edge, a first end, an intermediate portion, and a second end, said first end being adjacent to said right attachment member and said second end being adjacent to said left attachment member.

5. The viscosity measuring device defined in claim 4, wherein said base member further comprises:

a plurality of projecting portions, said projecting portions extending generally downwardly from said base member for cooperation with the upper edge of the open container of food substances, for proper positioning of the viscosity measuring device thereon.

6. The viscosity measuring device defined in claim 5, comprising:

first, second, and third projecting portions, said first projecting portion being positioned adjacent said first end of said base member, said second projecting portion being positioned adjacent said second end of said base member, and said third projecting portion being positioned along a rear edge of said intermediate portion of said base member.

7. The viscosity measuring device defined in claim 3, wherein the right and left attachment members include a position retaining mechanism whereby said housing may be adjustably retained in a fixed position relative to said base assembly.

8. The viscosity measuring device defined in claim 7, wherein said position retaining mechanism further comprises:

a ratchet tooth assembly including a multiplicity of generally vertically aligned ratchet teeth, each said ratchet tooth being selectively engageable with said position retaining mechanism.

9. The viscosity measuring device defined in claim 8, wherein said position retaining means mechanism comprises:

a spring member extending through and pivotally mounted to said housing, said spring member having first and second end portions engageable with ratchet tooth assemblies in said right and left attachment members, respectively, said spring member having a central portion; and a spring member controller externally actuable from a front side of said housing, said spring member controller being engageable with said central portion of said spring member, whereby applying pressure to said spring member controller causes said spring member to pivot within said housing, thereby disengaging said first and second end portions from said ratchet tooth assemblies, permitting the adjustment of the position of said housing relative to said base assembly.

10. The viscosity measuring device defined in claim 2, further comprising:

releasable attachment means for attachment of said probe member, said releasable attachment means being rotatably connected to said output portion of said motor.

11. The viscosity measuring device defined in claim 2, wherein said display comprises:

a plurality of light emitting diodes corresponding to various predetermined ranges of values as detected by said sensor.

12. The viscosity measuring device defined in claim 9, wherein said plurality of light emitting diodes includes first, second, third, and fourth light emitting diodes, each said diode relating to a unique range of values determined by said sensor.

13. The viscosity measuring device defined in claim 12, wherein said sensor is a microprocessor.

14. The viscosity measuring device defined in claim 2, wherein said sensor is a microprocessor.

15. The viscosity measuring device defined in claim 14, further comprising:

a calibration mechanism including a test button positioned on a front face of said housing for actuating a test cycle controlled by said microprocessor, wherein said motor is actuated causing said probe to rotate, until said microprocessor determines that said probe has reached a predetermined rotational velocity, said microprocessor then recording the operational characteristics of said motor when said probe is rotating at the predetermined rotational velocity.

16. The viscosity measuring device defined in claim 15, further comprising:

first visual indication means to indicate that said test cycle is underway.

17. The viscosity measuring device defined in claim 15, further comprising:

second visual indication means to indicate that said test cycle is complete.

18. The viscosity measuring device defined in claim 16, further comprising:

first audio indication means to indicate that said test cycle is complete.

19. The viscosity measurement device of claim 2, wherein the operational characteristics monitored by the sensor include a level of electrical energy required to drive the motor at a constant velocity.

20. The viscosity measurement device of claim 19, wherein monitoring of the electrical energy includes monitoring of the electrical current.

21. A viscosity measurement device for determining the viscosity of a food substance contained in an open container, comprising:

a housing;

a probe member extending from the lower surface of the housing for submersion into a portion of the food substance;

a motor cooperating with the probe to cause rotation of the probe; and a controller coupled to the motor for controlling the operation of the motor such that the probe rotates at a predetermined velocity, the controller further monitoring the motor to determine the amount of energy required by the motor to maintain the predetermined velocity and calculating a viscosity measurement of the food substance based upon the determined amount of energy.

22. The viscosity measurement device of claim 21, further comprising:

a base assembly associated with the housing which includes a lower surface which is configured to contact the open container, wherein the base assembly further comprises an adjustment mechanism for adjusting the position of the probe member relative to the lower surface.

23. The viscosity measurement device of claim 22, wherein the motor is contained within a housing body and the base assembly adjustment mechanism includes a right and left attachment member, each attachment member slidingly coupling the base assembly to the housing body.

24. The viscosity measurement device of claim 22, wherein the adjustment mechanism further comprises:

a locking mechanism; and a ratchet tooth assembly including a multiplicity of generally vertically aligned ratchet teeth, each of the ratchet teeth being selectively engageable with the locking mechanism.

25. The viscosity measurement device of claim 24, wherein the locking mechanism includes a lock button positioned on the exterior of the housing and a spring lever associated with the lock button such that operation of the lock button causes movement of the spring lever, the spring lever having an engaging portion which- engages with the ratchet teeth.

26. The viscosity measurement device of claim 21, wherein determining the amount of energy used by the motor comprises monitoring the electrical current used by the motor to operate at the predetermined velocity.

27. The viscosity measurement device of claim 21, wherein the controller does not calculate a viscosity measurement until the motor has operated at the predetermined velocity for a predetermined time.

28. The viscosity measurement device of claim 21, wherein the probe further comprises a detachable disposable portion.

29. The viscosity measurement device of claim 21, wherein the probe is detachable and disposable.

30. The viscosity measurement device of claim 21, wherein the probe is submerged a predetermined depth into the food substance prior to calculating the viscosity measurement.

31. The viscosity measurement device of claim 21, further comprising:

a calibration mechanism for actuating a calibration cycle prior to submersion of the probe into the food substance, the calibration mechanism including a test button positioned on the housing for initiating the calibration cycle wherein the motor is actuated causing the probe to rotate at the predetermined rotational velocity, the controller then recording the operational characteristics of said motor when the probe is rotating at the predetermined rotational velocity.

32. The viscosity measurement device of claim 31, wherein the viscosity measurement is calculated using the operational characteristics of the motor during the calibration cycle, and the operation characteristics of the motor when the probe is submerged into the food substance.

33. The viscosity measurement device of claim 21, wherein the probe is a cylindrical member.

* * * * *

UNITED STATES PATENT AND TRADEMARK OFFICE
CERTIFICATE OF CORRECTION

PATENT NO. : 6,145,373
DATED : 11/14/00
INVENTOR(S) : Donald L. Tymchuck

It is certified that error appears in the above-indentified patent and that said Letters Patent is hereby corrected as shown below:

Column 5, line 65, after the word "retaining" delete "means".
Column 7, line 35, after the word "which" delete "-".

Signed and Sealed this

Twenty-ninth Day of May, 2001

*Attest:*

NICHOLAS P. GODICI

*Attesting Officer*   *Acting Director of the United States Patent and Trademark Office*